(12) United States Patent
Yoshida et al.

(10) Patent No.: US 8,410,296 B2
(45) Date of Patent: *Apr. 2, 2013

(54) SURFACE TREATMENT AGENT AND SURFACE TREATMENT METHOD

(75) Inventors: Masaaki Yoshida, Kawasaki (JP); Mai Sugawara, Kawasaki (JP); Naohisa Ueno, Kawasaki (JP); Jun Koshiyama, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 117 days.

This patent is subject to a terminal disclaimer.

(21) Appl. No.: 12/943,466

(22) Filed: Nov. 10, 2010

(65) Prior Publication Data

US 2011/0118494 A1  May 19, 2011

(30) Foreign Application Priority Data

Nov. 13, 2009 (JP) ................... 2009-260401
Oct. 18, 2010 (JP) ................... 2010-233740

(51) Int. Cl.
*C07F 7/10* (2006.01)
(52) U.S. Cl. ...................... 556/409; 556/412
(58) Field of Classification Search .............. 556/409, 556/412
See application file for complete search history.

(56) References Cited

U.S. PATENT DOCUMENTS 7,081,673 B2 * 7/2006 Hedrick et al. ............... 257/751
2004/0137153 A1 * 7/2004 Thomas et al. ............... 427/384

FOREIGN PATENT DOCUMENTS

| JP | H06-163391 A | 6/1994 |
| JP | H07-142349 A | 6/1995 |
| JP | H11-511900 | 10/1999 |

OTHER PUBLICATIONS

Breed, L.W. et al, Synthesis of Elastomers containing Si-N bonds in the main chain, Defence Documentation Cener, AD 401789, Apr. 22, 1963.*

Higgins, P.R. et al, International Journal of Mass Spectrometry 210/211 (2001) 231-240.*

* cited by examiner

*Primary Examiner* — Sudhakar Katakam
*Assistant Examiner* — Pancham Bakshi
(74) *Attorney, Agent, or Firm* — Knobbe, Martens, Olson & Bear LLP

(57) ABSTRACT

Provided are a surface treatment agent for which hydrophobization to a high degree is possible even in a case of the material of a substrate surface being TiN or SiN, and surface treatment method using such a surface treatment agent. The surface treatment agent according to the present invention contains a cyclic silazane compound. As this cyclic silazane compound, a cyclic disilazane compound such as 2,2,5,5-tetramethyl-2,5-disila-1-azacyclopentane and 2,2,6,6-tetramethyl-2,6-disila-1-azacyclohexane and a cyclic trisilazane compound such as 2,2,4,4,6,6-hexamethylcyclotrisilazane and 2,4,6-trimethyl-2,4,6-trivinylcyclotrisilazane are preferred. In the surface treatment, a substrate surface is exposed to a surface treatment agent according to the present invention, and the substrate surface is hydrophobized.

8 Claims, No Drawings

SURFACE TREATMENT AGENT AND SURFACE TREATMENT METHOD

This application is based on and claims the benefit of priority from Japanese Patent Application Nos. 2009-260401 and 2010-233740, respectively filed on 13 Nov. 2009 and 18 Oct. 2010, the contents of which are incorporated herein by reference.

BACKGROUND OF THE INVENTION

1. Field of the Invention

The present invention relates to a surface treatment agent used in hydrophobization treatment of a substrate surface, and a surface treatment method using the same.

2. Related Art

In the production of semiconductor devices and the like, a lithography technique is applied when forming an inorganic pattern on a substrate. With this lithography technique, a photosensitive resin composition is used to provide a photosensitive resin layer on a substrate, then actinic radiation is selectively irradiated (exposed) to this, and a resin pattern (resist pattern) is formed on the substrate by performing a developing process. Then, an inorganic pattern is formed by etching the substrate with this resin pattern as a mask.

Incidentally, in recent years, trends in higher integration and miniaturization of semiconductor devices have grown, and thus progress towards miniaturization and higher aspect ratios of the inorganic patterns has advanced. However, a problem has arisen of so-called pattern collapse in the meantime. This pattern collapse is a phenomenon when forming several inorganic patterns on a substrate in parallel, in which adjacent patterns close in so as to lean on one another, and depending on the situation, the pattern becomes damaged and separate from the base. If such pattern collapse occurs, the desired product will not be obtained, thereby causing a decline in the yield and reliability of the product.

This pattern collapse is known to occur when drying a rinse liquid in a rinsing process after pattern formation, due to the surface tension of this rinse liquid. In fact, when the rinse liquid is removed in a drying step, stress based on the surface tension of the rinse liquid acts between patterns, whereby pattern collapse occurs.

Consequently, despite there having been numerous experiments thus far to prevent pattern collapse by adding a substance (isopropanol, fluorine-based surfactants, etc.) to the rinse liquid that causes the surface tension to decrease (e.g., refer to Patent Documents 1 and 2), the prevention of pattern collapse has been insufficient with the schemes of such rinse liquids.

Patent Document 1: Japanese Unexamined Patent Application Publication No. H6-163391
Patent Document 2: Japanese Unexamined Patent Application Publication No. H7-142349
Patent Document 3: Japanese Unexamined Patent Application Publication No. H11-511900

SUMMARY OF THE INVENTION

Incidentally, although different from pattern collapse, hydrophobization treatment using a silylation agent such as hexamethyldisilazane (HMDS) (silylation treatment) has been performed on substrate surfaces prior to providing a photosensitive resin layer on the substrate, in order to improve the adhesion between a resin pattern to be a mask and a substrate surface and prevent partial loss of the resin pattern from the developing solution (for example, refer to "Summary of the Invention" of Patent Document 3).

The present inventors have tried hydrophobization treatment on various substrates using several silylation agents such as HMDS and N,N-dimethylaminotrimethylsilane (DMATMS), believing that the force acting between patterns in a drying step after a rinse process could be reduced and pattern collapse could be prevented if the surface of the inorganic pattern were hydrophobized with a silylation agent. However, although hydrophobization to a high degree was possible in a case of the material of the substrate surface being Si, the extent of hydrophobization was insufficient with any silylation agent in a case of the material of the substrate surface being TiN or SiN.

The present invention was made taking this current situation into account, and has an object of providing a surface treatment agent that enables hydrophobization to a high degree even in a case of the material of a substrate surface being TiN or SiN, and a surface treatment method using such a surface treatment agent.

In order to solve the above-mentioned problems, the present inventors have conducted extensive studies. As a result thereof, they have found that the above-mentioned problem could be solved by using a cyclic silazane compound in the surface treatment agent, thereby arriving at completion of the present invention. More specifically, the present invention provides the following.

A first aspect of the present invention is a surface treatment agent that is used in hydrophobization treatment of a substrate surface, and contains a cyclic silazane compound.

A second aspect of the present invention is a surface treatment method of exposing a substrate surface to the surface treatment agent according to the present invention, and hydrophobizing the substrate surface.

According to the present invention, it is possible to highly hydrophobize a substrate surface, even in a case of the material of the substrate surface being TiN or SiN.

DETAILED DESCRIPTION OF THE INVENTION

Surface Treatment Agent

First, a surface treatment agent according to the present invention will be explained. The surface treatment agent according to the present invention is suitably used when hydrophobizing a substrate surface. Herein, a substrate used for semiconductor device manufacturing is exemplified as the "substrate". In addition, as well as the surface of the substrate itself, the surface of an inorganic pattern provided on the substrate, the surface of an inorganic layer that has not been patterned, or the like is exemplified as the "substrate surface".

As the inorganic pattern provided on the substrate, a pattern made by forming a resin pattern (resist pattern) on the surface of an inorganic layer present on the substrate using a lithography technique, and conducting an etching process on the inorganic layer with this resin pattern as a mask is exemplified. As well as the substrate itself, a film of an inorganic matter formed on the substrate surface or the like are exemplified as the inorganic layer.

In particular, the surface treatment agent according to the present invention is suitably used in a case of the material of the substrate surface being TiN or SiN. Conventionally, with a silylation agent such as hexamethyldisilazane (HMDS) used in hydrophobization of substrate surfaces, the extent of hydrophobization becomes insufficient in a case of the material of the substrate surface being TiN or SiN; however, according to the surface treatment agent according to the present invention, a substrate surface can be highly hydrophobized in a case of the material of the surface being TiN or SiN.

Since the surface treatment agent according to the present invention is vaporized by a means such as heating and bubbling, the vaporized surface treatment agent may be used to perform surface treatment by being made to contact the surface of a substrate, and may be used to perform surface treatment by coating the surface of the substrate in liquid form by a means such as a spin-coating method or dipping method.

The surface treatment agent according to the present invention contains a cyclic silazane compound as a silylation agent. The components contained in the surface treatment agent will be explained in detail hereinafter.

Cyclic Silazane Compound

The surface treatment agent according to the present invention contains a cyclic silazane compound as a silylation agent. This cyclic silazane compound is a component for silylating a substrate surface to raise the hydrophobicity of the substrate surface.

As this cyclic silazane compound, cyclic disilazane compounds such as 2,2,5,5-tetramethyl-2,5-disila-1-azacyclopentane and 2,2,6,6-tetramethyl-2,6-disila-1-azacyclohexane; cyclic trisilazane compounds such as 2,2,4,4,6,6-hexamethylcyclotrisilazane and 2,4,6-trimethyl-2,4,6-trivinylcyclotrisilazane; and cyclic tetrasilazane compounds such as 2,2,4,4,6,6,8,8-octamethylcyclotetrasilazane; and the like are exemplified.

Among these, in a case of the material of the substrate surface being TiN, cyclic disilazane compounds are preferred, and at least one among 2,2,5,5-tetramethyl-2,5-disila-1-azacyclopentane and 2,2,6,6-tetramethyl-2,6-disila-1-azacyclohexane is particularly preferred. As the cyclic disilazane compound, there are ones having a five-membered ring structure such as 2,2,5,5-tetramethyl-2,5-disila-1-azacyclopentane and ones having a six-membered ring structure such as 2,2,6,6-tetramethyl-2,6-disila-1-azacyclohexane; however, being a five-membered ring structure is more preferable.

On the other hand, in a case of the material of the substrate surface being SiN, a cyclic disilazane compound diluted in an organic solvent described later, or a cyclic trisilazane compound is preferred. As the cyclic disilazane compound diluted in an organic solvent, at least one among 2,2,5,5-tetramethyl-2,5-disila-1-azacyclopentane and 2,2,6,6-tetramethyl-2,6-disila-1-azacyclohexane is particularly preferred. In addition, as the cyclic trisilazane compound, at least one among 2,2,4,4,6,6-hexamethylcyclotrisilazane and 2,4,6-trimethyl-2,4,6-trivinylcyclotrisilazane is particularly preferred.

These cyclic silazane compounds can be used individually or by combining at least two thereof.

Organic Solvent

The surface treatment agent according to the present invention may further contain an organic solvent. By diluting the cyclic silazane compound with an organic solvent, it is possible to improve the coating workability on the substrate surface, handling ability, displaceability with the rinse liquid, etc. In addition, in a case of the material of the substrate surface being SiN, the extent of hydrophobicity can be raised by diluting a cyclic disilazane compound in an organic solvent.

So long as being able to dissolve the above-mentioned cyclic silazane compound without causing reaction with the above-mentioned cyclic silazane compound, and causing little damage to the substrate surface, a conventional well-known organic solvent can be used as this organic solvent without being particularly limited.

More specifically, sulfoxides such as dimethylsulfoxide; sulfones such as dimethylsulfone, diethylsulfone, bis(2-hydroxyethyl)sulfone and tetramethylenesulfone; amides such as N,N-dimethylformamide, N-methylformamide, N,N-dimethylacetamide, N-methylacetamide and N,N-diethylacetamide; lactams such as N-methyl-2-pyrrolidone, N-ethyl-2-pyrrolidone, N-propyl-2-pyrrolidone, N-hydroxymethyl-2-pyrrolidone and N-hydroxyethyl-2-pyrrolidone; imidazolidinones such as 1,3-dimethyl-2-imidazolidinone, 1,3-diethyl-2-imidazolidinone and 1,3-diisopropyl-2-imidazolidinone; (poly)alkylene glycol alkyl ethers such as ethylene glycol monomethyl ether, ethylene glycol monoethyl ether, diethylene glycol monomethyl ether, diethylene glycol monoethyl ether, triethylene glycol monomethyl ether, triethylene glycol monoethyl ether, propylene glycol monomethyl ether, propylene glycol monoethyl ether, dipropylene glycol monomethyl ether, dipropylene glycol monoethyl ether, tripropylene glycol monomethyl ether, ethylene glycol dimethyl ether, ethylene glycol diethyl ether, diethylene glycol dimethyl ether, diethylene glycol methyl ethyl ether, diethylene glycol diethyl ether and triethylene glycol dimethyl ether; (poly)alkylene glycol alkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate and propylene glycol monoethyl ether acetate; other esters such as tetrahydrofuran; ketones such as methyl ethyl ketone, cyclohexanone, 2-heptanone and 3-heptanone; alkyl lactate esters such as 2-hydroxypropanoic acid methyl and 2-hydroxypropanoic acid ethyl; other esters such as 3-methoxypropanoic acid methyl, 3-methoxypropanoic acid ethyl, 3-ethoxypropanoic acid methyl, 3-ethoxypropanoic acid ethyl, ethoxyacetic acid ethyl, 3-methyl-3-methoxybutyl acetate, 3-methyl-3-methoxybutyl propionate, ethyl acetate, n-propyl acetate, i-propyl acetate, n-butyl acetate, i-butyl acetate, n-pentyl formate, i-pentyl acetate, n-butyl propionate, ethyl butyrate, n-propyl butyrate, i-propyl butyrate, n-butyl butyrate, methyl pyruvate, ethyl pyruvate, n-propyl pyruvate, methyl acetoacetate, ethyl acetoacetate and ethyl 2-oxobutanoate; lactones such as β-propiolactone, γ-butyrolactone and δ-pentyrolactone; straight chain, branched chain or cyclic hydrocarbons such as n-hexane, n-heptane, n-octane, n-nonane, methyloctane, n-decane, n-undecane, n-dodecane, 2,2,4,6,6-pentamethyl heptane, 2,2,4,4,6,8,8-heptamethyl nonane, cylcohexane and methylcyclohexane; aromatic hydrocarbons such as benzene, toluene, naphthalene and 1,3,5-trimethyl benzene; terpenes such as p-menthane, diphenyl methane, limonene, terpinene, bornane, norbornane and pinane; and the like can be exemplified. These organic solvents can be used individually or by mixing at least two thereof.

In a case of diluting the cyclic silazane compound with an organic solvent, the concentration of the cyclic silazane compound in the surface treatment agent is preferably 0.1 to 99.9% by mass, is more preferably 1 to 50% by mass, is further preferably 1 to 30% by mass, and particularly preferably 3 to 20% by mass. By setting to the above-mentioned ranges, it is possible to raise the coating workability on the substrate surface, the handling ability, and the displaceability with the rinse liquid, while preserving the effects of the surface treatment. It should be noted that, in a case of using a cyclic trisilazane compound as the cyclic silazane compound, it is generally preferable to set to a higher concentration than in a case of using a cyclic disilazane compound.

The timing of diluting the cyclic silazane compound with an organic solvent is not particularly limited. For example, the cyclic silazane compound may be store in a state diluted with an organic solvent in advance, or may be configured so as to dilute the cyclic silazane compound with an organic solvent immediately prior to treating a substrate surface using the surface treatment agent.

Surface Treatment Method

Next, a surface treatment method according to the present invention will be explained. The surface treatment method according to the present invention exposes a substrate surface to the surface treatment agent according to the present invention, and treats the surface of this substrate.

The surface treatment method according to the present invention hydrophobizes a substrate surface, and the object of this treatment may be anything; however, as a representative example of the object of this treatment, (1) to hydrophobize a substrate surface to improve the adhesion to a resin pattern composed of photoresist or the like, and (2) to prevent pattern collapse of an inorganic pattern or resin pattern on a substrate surface in a drying step after rinsing can be given.

In the case of having the above-mentioned (1) as an object, prior to forming a photosensitive resin layer on the substrate surface, for example, the surface of the substrate may be exposed to the surface treatment agent according to the present invention. As the method of exposing the substrate surface to the surface treatment agent according to the present invention, a conventional well-known method can be used without being particularly limited. For example, a method of vaporizing the surface treatment agent according to the present invention to form vapor and causing this vapor to contact the substrate surface, a method of causing the surface treatment agent according to the present invention to contact the substrate surface by a spin-coating method, immersion method, etc. can be exemplified. Since the hydrophobicity of the substrate surface is improved by such an operation, the adhesion to a photosensitive resin layer or the like is improved.

In the case of having the above-mentioned (2) as an object, prior to performing post-rinse process drying after an inorganic layer has been formed, the substrate surface may be exposed to the surface treatment agent according to the present invention.

The reason that pattern collapse of an inorganic pattern on a substrate surface can be prevented in a drying step after rinsing by conducting such a surface treatment will be explained.

When forming an inorganic pattern on a substrate surface, dry etching or wet etching is performed, for example. In pattern formation by dry etching, dry etching is performed by way of a halogen series gas or the like, then etching residue such as particles and metallic impurities is washed with SC-1 (ammonia/hydrogen peroxide solution), SC-2 (hydrochloric acid/hydrogen peroxide solution), or the like. Then, after rinsing using a rinse liquid such as water and isopropanol, the surface of the inorganic pattern is dried by air drying, spin drying, or the like. On the other hand, in pattern formation by wet etching, wet etching is performed using DHF (dilute hydrofluoric acid), BHF (hydrofluoric acid/ammonium fluoride), SPM (sulfuric acid/hydrogen peroxide solution), APM (ammonia/hydrogen peroxide solution), or the like, and after rinsing using a rinse liquid such as water and isopropanol, the surface of the inorganic pattern is dried by air drying, spin drying, or the like.

It should be noted that a method such as that described starting from paragraph 0030 of Japanese Patent No. 3866130, for example, is acceptable as the drying process.

In the surface treatment method according to the present invention, prior to drying such an inorganic pattern, the inorganic pattern surface is hydrophobized by treating with the surface treatment agent according to the present invention.

Herein, the force F acting between the patterns of the inorganic pattern in the drying step after rinsing is represented as in the following formula (I). In the formula, $\gamma$ represents the surface tension of the rinse liquid, $\theta$ represents the contact angle of the rinse liquid, A represents the aspect ratio of the inorganic pattern, and D represents the distance between the inorganic pattern side walls.

$$F = 2\gamma \cdot \cos \theta A/D \quad (I)$$

Therefore, if the surface of the inorganic pattern can be hydrophobized and the contact angle of the rinse liquid increased ($\cos \theta$ reduced), the force acting between the inorganic patterns in the drying step following rinsing can be reduced, and thus pattern collapse can be prevented.

This surface treatment is performed by immersing the substrate on which an inorganic pattern has been formed in the surface treatment agent, or by coating or spraying the surface treatment agent on the inorganic pattern. The treatment time is preferably 10 seconds to 60 minutes. In addition, after this surface treatment, the contact angle of water on the inorganic pattern surface preferably becomes 60 to 120 degrees, more preferably becomes 75 to 105 degrees, and further preferably 80 to 100 degrees.

EXAMPLES

Although the present invention will be explained more specifically by way of Examples hereinafter, the present invention is not to be limited to the following Examples.

Example 1 and Comparative Examples 1 and 2

After having washed a substrate in which the material of the surface is TiN for 3 minutes with a 0.1% hydrogen fluoride aqueous solution, it was immersed in 2,2,5,5-tetramethyl-2,5-disila-1-azacyclopentane (TDACP), hexamethyldisilazane (HMDS), or N,N-dimethylamino trimethylsilane (DMATMS) for 30 seconds at room temperature. Then, the substrate surface was rinsed with methyl ethyl ketone, and made to dry by way of blowing nitrogen thereon. Thereafter, using a Dropmaster 700 (Kyowa Interface Science Co., Ltd.), a droplet of pure water (1.8 μL) was dropped on the substrate surface, and the contact angle was measured 10 seconds after dropping. The results are shown in Table 1. It should be noted that the contact angle listed in Table 1 as "TiN comparison" is a numerical value of a contact angle of a substrate surface to which the surface treatment had not been conducted.

Example 2 and Comparative Examples 3 and 4

After having washed a substrate in which the material of the surface is SiN for 3 minutes with a 0.1% hydrogen fluoride aqueous solution, it was immersed in 2,2,4,4,6,6-hexamethylcyclotrisilazane (HMCTS), hexamethyldisilazane (HMDS), or N,N-dimethylamino trimethylsilane (DMATMS) for 30 seconds at room temperature. Then, the substrate surface was rinsed with methyl ethyl ketone, and made to dry by way of blowing nitrogen thereon. Thereafter, using a Dropmaster 700 (Kyowa Interface Science Co., Ltd.), a droplet of pure water (1.8 μL) was dropped on the substrate surface, and the contact angle was measured 10 seconds after dropping. The results are shown in Table 1. It should be noted that the contact angle listed in Table 1 as "SiN comparison" is a numerical value of a contact angle of a substrate surface to which the surface treatment had not been conducted.

Reference Examples 1 to 4

Except for using a substrate in which the material of the surface is Si, the contact angle of the substrate surface was measured similarly to above. The results are shown in Table 1. It should be noted that the contact angle listed in Table 1 as "Si comparison" is a numerical value of the contact angle of a substrate surface to which the surface treatment had not been conducted.

TABLE 1

|  | Substrate Surface | Surface Treatment Agent | Contact Angle (degrees) |
| --- | --- | --- | --- |
| Example 1 | TiN | TDACP | 83 |
| Comparative Example 1 | TiN | HMDS | 69 |
| Comparative Example 2 | TiN | DMATMS | 59 |
| TiN comparison | TiN | — | 28 |
| Example 2 | SiN | HMCTS | 85 |
| Comparative Example 3 | SiN | HMDS | 53 |
| Comparative Example 4 | SiN | DMATMS | 65 |
| SiN comparison | SiN | — | 45 |
| Reference Example 1 | Si | TDACP | 89 |
| Reference Example 2 | Si | HMCTS | 82 |
| Reference Example 3 | Si | HMDS | 79 |
| Reference Example 4 | Si | DMATMS | 93 |
| Si comparison | Si | — | 22 |

As is evident from Table 1, a high contact angle of 83 degrees could be realized with Example 1 using TDACP, which is a cyclic silazane compound, as the surface treatment agent, even in a case of the material of the substrate surface being TiN. On the other hand, the contact angle was 69 degrees with Comparative Example 1 using HMDS as the surface treatment agent, and the contact angle was 59 degrees with Comparative Example 2 using DMATMS as the surface treatment agent, both being far inferior to Example 1.

In addition, a high contact angle of 85 degrees could be realized with Example 2 using HMCTS, which is a cyclic silazane compound, as the surface treatment agent, even in a case of the material of the substrate surface being SiN. On the other hand, the contact angle was 53 degrees with Comparative Example 3 using HMDS as the surface treatment agent, and the contact angle was 65 degrees with Comparative Example 4 using DMATMS as the surface treatment agent, both being far inferior to Example 2.

It should be noted that a high contact angle of at least 79 degrees could be realized by any of the surface treatment agents in a case of the material of the substrate surface being Si.

Examples 3 to 17 and Comparative Examples 5 to 11

After having washed a substrate in which the material of the surface is Si, SiN or TiN for 3 minutes with a 0.1% hydrogen fluoride aqueous solution, it was further washed with isopropanol. Thereafter, it was immersed for 30 seconds at room temperature in a surface treatment agent in which 2,2,5,5-tetramethyl-2,5-disila-1-azacyclopentane (TDACP), 2,2,4,4,6,6-hexamethylcyclotrisilazane (HMCTS), hexamethyldisilazane (HMDS), or N,N-dimethylaminotrimethylsilane (DMATMS) had been diluted in an appropriate organic solvent. Then, the substrate surface was rinsed with isopropanol, followed by water, and then dried by blowing nitrogen thereon. Thereafter, using a Dropmaster 700 (Kyowa Interface Science Co., Ltd.), a droplet of pure water (1.8 μL) was dropped on the substrate surface, and the contact angle was measured 10 seconds after dropping. The results are shown in Table 2.

TABLE 2

|  | Silylation Agent | Organic Solvent | Silylation Agent Concentration (% by mass) | Contact Angle (degrees) | | |
| --- | --- | --- | --- | --- | --- | --- |
|  |  |  |  | Si | SiN | TiN |
| Example 3 | TDACP | — | 100 | 89.4 | 57.7 | 99.3 |
| Example 4 | TDACP | n-heptane | 3 | 90.1 | 66.9 | 67.0 |
| Example 5 | TDACP | n-heptane | 5 | 90.6 | 67.1 | 67.1 |
| Example 6 | TDACP | n-heptane/PM = 50/50 | 20 | 92.8 | 68.3 | 69.3 |
| Example 7 | TDACP | n-octane | 5 | 91.9 | 60.2 | 66.1 |
| Example 8 | TDACP | n-nonane | 5 | 90.8 | 66.6 | 80.6 |
| Example 9 | TDACP | n-decane | 5 | 80.6 | 77.6 | 82.2 |
| Example 10 | TDACP | n-decane | 10 | 88.1 | 83.7 | 85.4 |
| Example 11 | TDACP | PM | 5 | 101.2 | 78.1 | 73.0 |
| Example 12 | TDACP | GBL | 3 | 97.1 | 89.5 | 83.2 |
| Example 13 | TDACP | GBL | 15 | 97.8 | 90.1 | 83.8 |
| Example 14 | TDACP | DEG | 10 | 89.8 | 76.4 | 83.7 |
| Example 15 | TDACP | DMDG | 10 | 92.2 | 75.2 | 86.5 |
| Example 16 | TDACP | DMTG | 10 | 84.2 | 76.4 | 72.0 |
| Example 17 | HMCTS | n-decane | 20 | 89.5 | 63.0 | 73.0 |
| Comparative Example 5 | HMDS | — | 100 | 81.4 | 43.3 | 14.4 |
| Comparative Example 6 | HMDS | GBL | 3 | 96.4 | 45.0 | 64.6 |
| Comparative Example 7 | HMDS | n-decane | 5 | 77.6 | 30.4 | 30.0 |
| Comparative Example 8 | DMATMS | GBL | 3 | 93.0 | 55.0 | 19.1 |
| Comparative Example 9 | DMATMS | PM | 5 | 93.5 | 54.1 | 17.4 |
| Comparative Example 10 | DMATMS | n-heptane | 3 | 91.9 | 32.2 | 12.5 |
| Comparative Example 11 | DMATMS | n-decane | 5 | 94.5 | 55.3 | 40.6 |

PM: propylene glycol monomethyl ether acetate
GBL: γ-butyrolactone
DEG: ethylene glycol diethyl ether
DMDG: diethylene glycol dimethyl ether
DMTG: triethylene glycol dimethyl ether As is evident from Table 2, the substrate surface could be highly hydrophobized with Examples 4 to 17 using a surface treatment agent in which TDACP or HMCTS, which are cyclic silazane compounds, were diluted in an organic solvent, even in a case of the material of the substrate surface being SiN or TiN. As is evident from comparing Example 3 with Examples 4 to 16, the substrate surface that was SiN could be more highly hydrophobized in the case of diluting TDACP, which is a cyclic disilazane compound, in an organic solvent than the case of not diluting in an organic solvent.

On the other hand, although hydrophobization to a high degree was possible in the case of the material of the substrate surface being Si with Comparative Examples 6 to 11 using a surface treatment agent in which HMDS or DMATMS was diluted in an organic solvent, the extent of hydrophobization was insufficient in the case of the material of the substrate surface being SiN or TiN. In addition, as is evident from comparing Comparative Example 5 with Comparatives Examples 6 and 7, the extent of hydrophobization for the substrate surface of SiN was not improved even when diluting HMDS in an organic solvent.

What is claimed is:

1. A surface treatment method comprising:
exposing a substrate surface to a surface treatment agent comprising a cyclic silazane compound so as to hydrophobize the substrate surface, wherein a material of the substrate surface is TiN or SiN.

2. The surface treatment method according to claim 1, wherein the cyclic silazane compound is a cyclic disilazane compound or a cyclic trisilazane compound.

3. The surface treatment method according to claim 2, wherein the cyclic disilazane compound is at least one selected from the group consisting of 2,2,5,5-tetramethyl-2,5-disila-1-azacyclopentane and 2,2,6,6-tetramethyl-2,6-disila-1-azacyclohexane.

4. The surface treatment method according to claim 2, wherein the cyclic trisilazane compound is at least one selected from the group consisting of 2,2,4,4,6,6-hexamethylcyclotrisilazane and 2,4,6-trimethyl-2,4,6-trivinylcyclotrisilazane.

5. The surface treatment method according to claim 1, wherein the surface treatment agent consists essentially of said cyclic silazane compound.

6. The surface treatment method according to claim 1, wherein the method consists essentially of said exposing.

7. The surface treatment method according to claim 6, further comprising rinsing the surface after said exposing.

8. The surface treatment method according to claim 7, further comprising drying the rinsed surface.

* * * * *